(12) United States Patent
Cawley et al.

(10) Patent No.: US 8,512,382 B2
(45) Date of Patent: Aug. 20, 2013

(54) MONOAXIAL AND POLYAXIAL PEDICLE SCREW

(75) Inventors: Trace Cawley, Boca Raton, FL (US); Chester Sharps, Manakin-Sabot, VA (US); Hans Robert Tuten, Richmond, VA (US)

(73) Assignee: US Spine, Inc., Salt Lake City, UT (US)

( * ) Notice: Subject to any disclaimer, the term of this patent is extended or adjusted under 35 U.S.C. 154(b) by 627 days.

(21) Appl. No.: 12/578,690

(22) Filed: Oct. 14, 2009

(65) Prior Publication Data

US 2010/0094354 A1   Apr. 15, 2010

Related U.S. Application Data

(60) Provisional application No. 61/105,079, filed on Oct. 14, 2008.

(51) Int. Cl.
*A61B 17/70* (2006.01)

(52) U.S. Cl.
USPC ........... 606/265; 606/270; 606/272; 606/301; 606/302

(58) Field of Classification Search
USPC .......................................... 606/265–270, 272
See application file for complete search history.

(56) References Cited

U.S. PATENT DOCUMENTS

| | | | |
|---|---|---|---|
| 5,562,663 A * | 10/1996 | Wisnewski et al. | 606/250 |
| 6,540,749 B2 * | 4/2003 | Schafer et al. | 606/270 |
| 7,896,902 B2 * | 3/2011 | Jeon et al. | 606/246 |
| 2005/0203516 A1 * | 9/2005 | Biedermann et al. | 606/61 |
| 2005/0277927 A1 * | 12/2005 | Guenther et al. | 606/61 |

* cited by examiner

*Primary Examiner* — Nicholas Woodall
(74) *Attorney, Agent, or Firm* — Phillips Ryther & Winchester; Matthew D. Thayne

(57) ABSTRACT

The present invention relates to an alternatively monoaxial and polyaxial pedicle or other similar surgical screw that can be used in a polyaxial manner and then locked or otherwise secured at a desired angle or orientation, i.e. used in a monoaxial manner, prior to engaging a rod or other similar stabilization member with the pedicle or other similar surgical screw. In other words, the present invention provides a pedicle or other similar surgical screw that can be selectively used in either a monoaxial or polyaxial configuration, as is desirable in a particular application or at a particular point of a given surgical procedure.

31 Claims, 4 Drawing Sheets

MONOAXIAL AND POLYAXIAL PEDICLE SCREW

CROSS-REFERENCE TO RELATED APPLICATION(S)

The present non-provisional patent application/patent claims the benefit of priority of U.S. Provisional Patent Application No. 61/105,079, filed on Oct. 14, 2008, and entitled "MONOAXIAL AND POLYAXIAL PEDICLE SCREW," the contents of which are incorporated in full by reference herein.

FIELD OF THE INVENTION

The present invention relates generally to spinal and other similar surgical implant devices and associated surgical methods. More specifically, the present invention relates to an alternatively monoaxial and polyaxial pedicle or other similar surgical screw that can be used in a polyaxial manner and then locked or otherwise secured at a desired angle or orientation, i.e. used in a monoaxial manner, prior to engaging a rod or other similar stabilization member with the pedicle or other similar surgical screw. In other words, the present invention provides a pedicle or other similar surgical screw that can be selectively used in either a monoaxial or polyaxial configuration, as is desirable in a particular application or at a particular point of a given surgical procedure.

BACKGROUND OF THE INVENTION

When confronted with various spinal diseases, injuries, and conditions, it is often desirable for a spinal surgeon to perform an interbody fusion or the like, whereby adjacent vertebrae are fused together using a bone graft and/or an implantable device, or otherwise immobilize a portion of the spine of a patient, either temporarily or permanently. Typically, in the interbody fusion case, the adjacent vertebrae are immobilized while the bone graft is allowed to "take," for example, using a conventional pedicle screw system, a plate system, or the like. Such a pedicle screw system consists of a plurality of pedicle screws that are anchored to adjacent levels of the spine and connected with stabilizing rods or the like. Such a plate system consists of a plate that is anchored to adjacent levels of the spine and, optionally, connected to the implantable device. Another potential option when treating various spinal diseases and injuries is to immobilize the associated facet joint(s) using one or more facet bolts or the like. In order to accomplish this, the superior and inferior facets to be joined must be aligned and securely held during drilling and bolt placement, for example. It is also sometimes desirable that they are compressed either before or during drilling and bolt placement.

Conventional pedicle screw systems consisting of a plurality of pedicle screws that are anchored to adjacent levels of the spine and connected with stabilizing rods or the like, typically utilize pedicle screws that are exclusively monoaxial or polyaxial. These monoaxial pedicle screws, which have a rod-receiving head that is fixed in orientation in relation to the threaded portion of the screw, disadvantageously must initially be placed in precise alignment with the pedicle or other bony structure in which they are disposed and provide little subsequent flexibility. The alignment of the engaged rod is set by the initial placement and orientation of the screw. These polyaxial pedicle screws, which have a rod-receiving head that is movable in orientation in relation to the threaded portion of the screw, disadvantageously must be placed in a desired alignment simultaneous with rod placement and often provide too much flexibility. The alignment of the engaged rod is not set until the rod is placed and secured. Both types of pedicle screws typically utilize one or more set screws to provide pressure on the rod, which in turn provides pressure on the head of the pedicle screw. What is often needed in the art is a pedicle screw system, or other surgical screw system, that allows the threaded portion of the screw to be secured in a bony structure, the angle and orientation of the head to be subsequently selected and secured, and then the placement and securement of the stabilization structure performed. In other words, what is often needed is a polyaxial-to-monoaxial screw system.

BRIEF SUMMARY OF THE INVENTION

In various exemplary embodiments, the present invention relates to an alternatively monoaxial and polyaxial pedicle or other similar surgical screw that can be used in a polyaxial manner and then locked or otherwise secured at a desired angle or orientation, i.e. used in a monoaxial manner, prior to engaging a rod or other similar stabilization member with the pedicle or other similar surgical screw. In other words, the present invention provides a pedicle or other similar surgical screw that can be selectively used in either a monoaxial or polyaxial configuration, as is desirable in a particular application or at a particular point of a given surgical procedure.

In one exemplary embodiment of the present invention, a surgical screw system includes: a surgical screw including a head portion and a threaded portion; a compressible sheath disposed about at least a portion of the head portion of the surgical screw; a tulip assembly, wherein the head portion of the surgical screw is disposed within the tulip assembly; and a compression structure disposed within the tulip assembly, wherein the compression structure is operable for selectively compressing the compressible sheath about the head portion of the surgical screw, thereby securing the head portion of the surgical screw in place within the tulip assembly. Optionally, the head portion of the surgical screw has a substantially spherical shape and the compressible sheath has an at least partially substantially spherical shape. The surgical screw system also includes a stabilizing member disposed partially within the tulip assembly and having a primary axis substantially perpendicular to the primary axis of the threaded portion of the surgical screw. Optionally, the compression structure is disposed concentrically within the tulip assembly on opposing sides of the stabilizing member. The surgical screw system further includes an outer set screw threadedly disposed within the tulip assembly, wherein the outer set screw is operable for selectively compressing the compression structure against the compressible sheath and the compressible sheath about the head portion of the surgical screw, thereby securing the head portion of the surgical screw in place within the tulip assembly. The surgical screw system still further includes an inner set screw threadedly disposed with the outer set screw, wherein the inner set screw is operable for selectively securing the stabilizing member in place within the tulip assembly.

In another exemplary embodiment of the present invention, a method for providing a surgical screw system includes: providing a surgical screw including a head portion and a threaded portion; providing a compressible sheath disposed about at least a portion of the head portion of the surgical screw; providing a tulip assembly, wherein the head portion of the surgical screw is disposed within the tulip assembly; and providing a compression structure disposed within the tulip assembly, wherein the compression structure is operable for selectively compressing the compressible sheath about the head portion of the surgical screw, thereby securing the head portion of the surgical screw in place within the tulip assembly. Optionally, the head portion of the surgical screw has a substantially spherical shape and the compressible sheath has an at least partially substantially spherical shape. The method for providing the surgical screw system also includes providing a stabilizing member disposed partially within the tulip assembly and having a primary axis substantially perpendicular to the primary axis of the threaded portion of the surgical screw. Optionally, the compression structure is disposed concentrically within the tulip assembly on opposing sides of the stabilizing member. The method for providing the surgical screw system further includes providing an outer set screw threadedly disposed within the tulip assembly, wherein the outer set screw is operable for selectively compressing the compression structure against the compressible sheath and the compressible sheath about the head portion of the surgical screw, thereby securing the head portion of the surgical screw in place within the tulip assembly. The method for providing the surgical screw system still further includes providing an inner set screw threadedly disposed with the outer set screw, wherein the inner set screw is operable for selectively securing the stabilizing member in place within the tulip assembly.

In a further exemplary embodiment of the present invention, a pedicle screw system includes: a pedicle screw including a head portion and a threaded portion; a compressible cup disposed about at least a portion of the head portion of the pedicle screw; a tulip assembly, wherein the head portion of the pedicle screw is disposed within the tulip assembly; and a compressible wedge member disposed within the tulip assembly, wherein the compressible wedge member is operable for selectively compressing the compressible cup about the head portion of the pedicle screw, thereby securing the head portion of the pedicle screw in place within the tulip assembly. Optionally, the head portion of the pedicle screw has a substantially spherical shape and the compressible cup has an at least partially substantially spherical shape. The pedicle screw system also includes a stabilizing member disposed partially within the tulip assembly and having a primary axis substantially perpendicular to the primary axis of the threaded portion of the pedicle screw. Optionally, the compressible wedge member is disposed concentrically within the tulip assembly on opposing sides of the stabilizing member. The pedicle screw system further includes an outer set screw threadedly disposed within the tulip assembly, wherein the outer set screw is operable for selectively compressing the compressible wedge member against the compressible cup and the compressible cup about the head portion of the pedicle screw, thereby securing the head portion of the pedicle screw in place within the tulip assembly. The pedicle screw system still further includes an inner set screw threadedly disposed with the outer set screw, wherein the inner set screw is operable for selectively securing the stabilizing member in place within the tulip assembly.

BRIEF DESCRIPTION OF THE DRAWINGS

The present invention is illustrated and described herein with reference to the various drawings, in which like reference numbers are used to denote like system components/method steps, as appropriate, and in which.

DETAILED DESCRIPTION OF THE INVENTION

In various exemplary embodiments, the present invention relates to an alternatively monoaxial and polyaxial pedicle or other similar surgical screw that can be used in a polyaxial manner and then locked or otherwise secured at a desired angle or orientation, i.e. used in a monoaxial manner, prior to engaging a rod or other similar stabilization member with the pedicle or other similar surgical screw. In other words, the present invention provides a pedicle or other similar surgical screw that can be selectively used in either a monoaxial or polyaxial configuration, as is desirable in a particular application or at a particular point of a given surgical procedure. The pedicle screw includes a set screw that is configured to selectively compress a wedge structure, which then compresses a compressible cup, which then impinges on a head portion of the pedicle screw, thereby locking the "tulip" portion of the pedicle screw at a desired angle and orientation with respect to the threaded portion of the pedicle screw.

Figure 1:
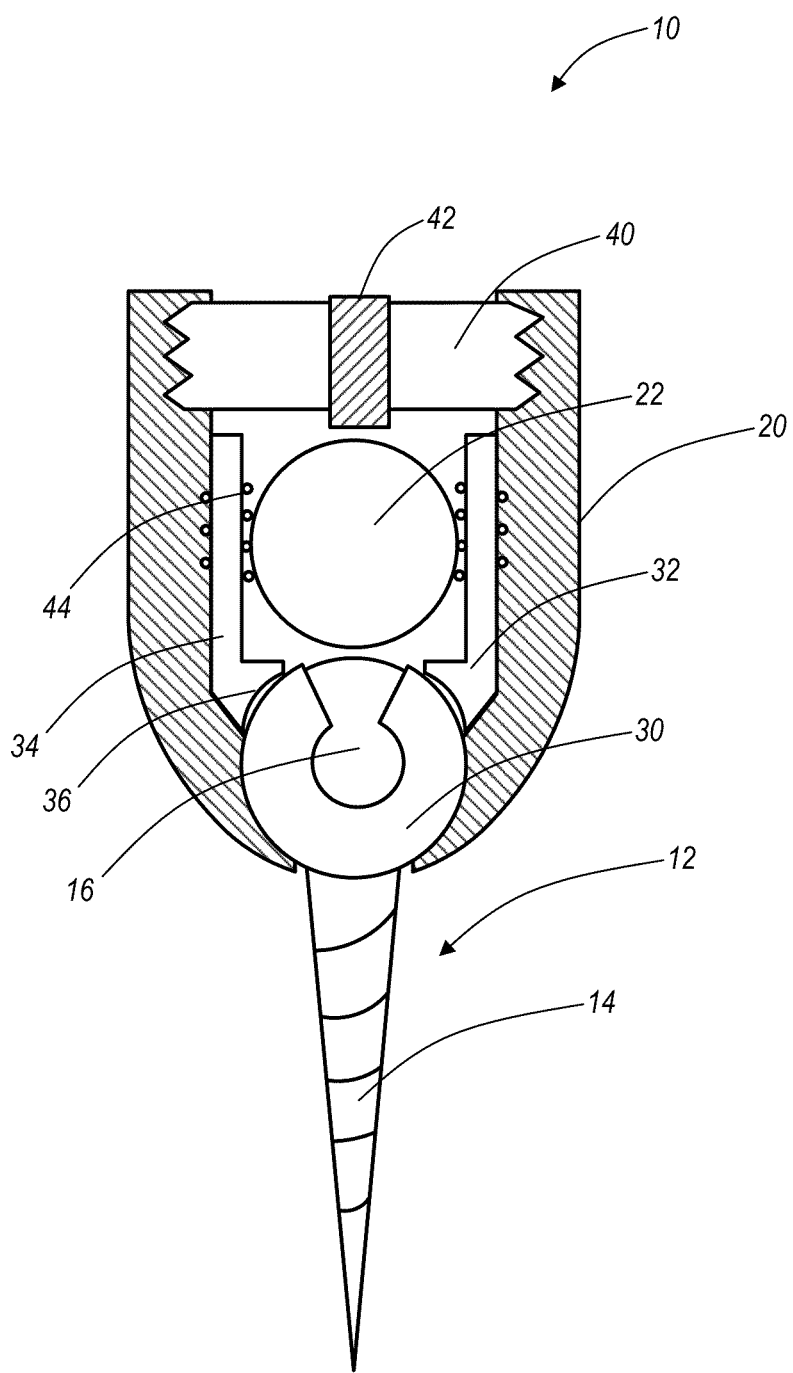
FIG. 1 is a partial cross-sectional diagram of a pedicle or other surgical screw system, according to one exemplary embodiment of the present invention.
Figure 2:
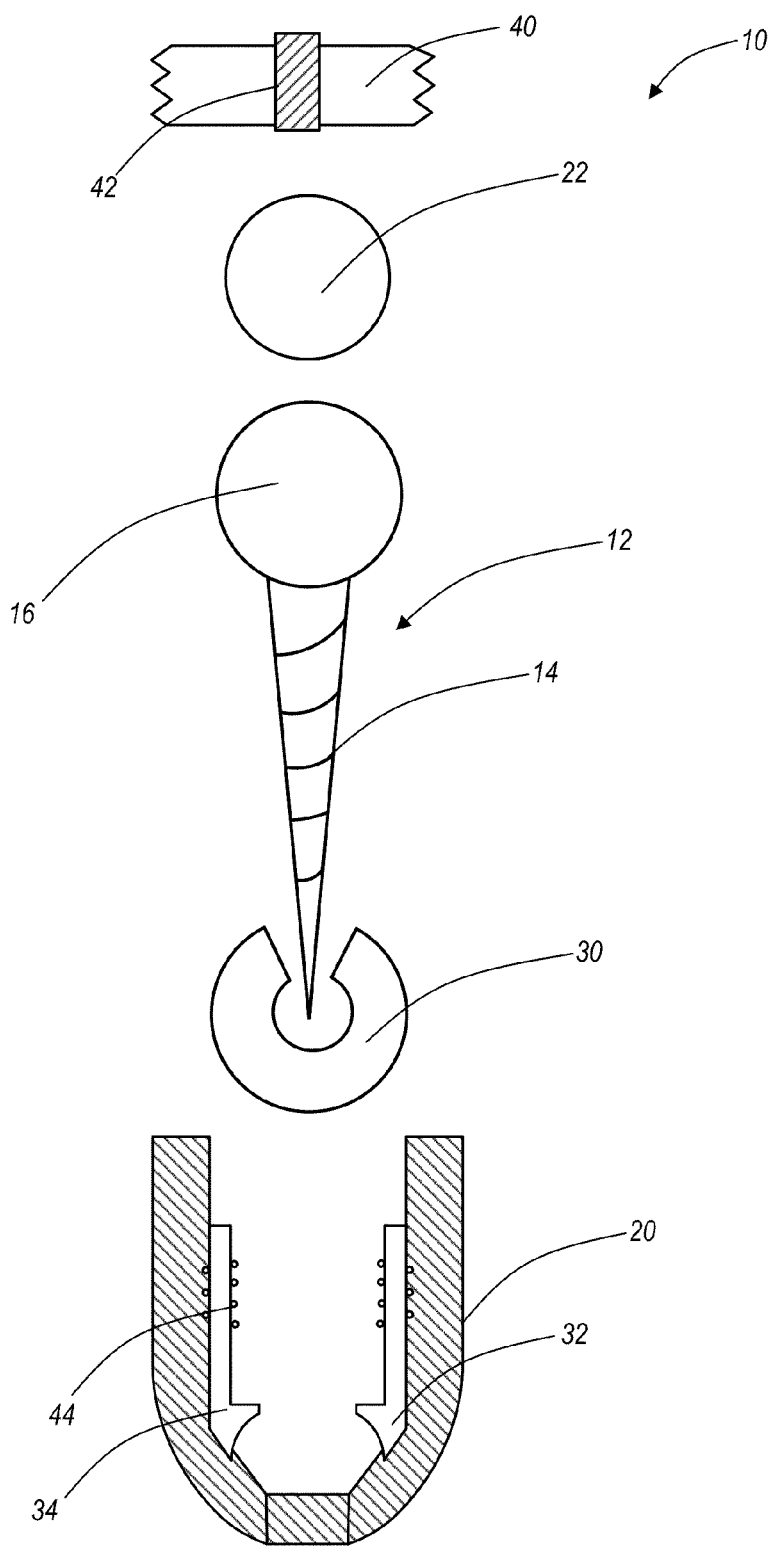
FIG. 2 is a partial cross-sectional exploded diagram of the pedicle or other surgical screw system of FIG. 1, according to one exemplary embodiment of the present invention.

Referring to FIGS. 1 and 2, a pedicle screw system 10 is illustrated according to one exemplary embodiment of the present invention. It will be readily apparent to those of ordinary skill in the art that the concepts illustrated and described herein can be extended to other surgical screw systems as well, provided that such surgical screw systems utilize surgical screws that have a "tulip" portion through which a stabilizing member is selectively disposed and secured and a threaded portion. The pedicle screw system 10 includes a pedicle screw 12 that includes a bone screw 14 and a screw head 16. The pedicle screw 12 is configured to be selectively screwed into a bony anatomical structure of a patient, such as a pedicle of the spine or the like. Thus, the bone screw 14 includes appropriate threads or the like and the screw head 16 includes recesses or the like for engaging a driver tool, etc.

The pedicle screw system 10 further includes a tulip assembly 20 concentrically formed/disposed around the screw head 16, with the bone screw 14 protruding through downwardly through the bottom thereof. The tulip assembly 20 is configured to selectively fix (i.e. secure) a longitudinal stabilizing member 22 to the pedicle screw 12 at a desired angle and orientation. Typically, the stabilizing member 22 includes an elongate rod that is inserted through opposed openings manufactured into either side of the tulip assembly 20, the elongate rod oriented substantially perpendicular to the axis of the pedicle screw 12. Often, the elongate rod will physically contact the screw head 16.

The pedicle screw system 10 of the present invention also includes a compressible cup 30 or other sleeve structure disposed about the screw head 16. The screw head 16 rests snugly inside the compressible cup 30 or other sleeve structure. Preferably, the tulip assembly 20 includes wedges 32, 34 disposed within the interior of the tulip assembly 20. The wedges 32, 34 extend substantially from the top of the tulip assembly 20 downwards towards the compressible cup 30 or other sleeve structure. The wedges 32, 34 can be separate components or integrally formed. For example, the wedges 32, 34 can be joined at a common ring at their top ends, etc. At the compressible cup 30 or other sleeve structure, the wedges 32, 34 have a shape 36 that is configured to conformally mate with the surface of the compressible cup 30 or other sleeve structure.

The tulip assembly 20 also includes an outer set screw 40 that is externally threaded and is operable to screw into the tulip assembly 20, which is internally threaded, and exert a compressive force upon the tops of the wedges 32, 34. Correspondingly, the wedges 32, 34 compress the compressible cup 30 or other sleeve structure around the screw head 16, thereby "locking" the tulip assembly 20 to the pedicle screw 12 through the screw head 16. In other words, the outer set screw 40 drives the wedges 32, 34 into the compressible cup 30 or other sleeve structure, which exerts compressive force on the screw head 16, thereby securing the angle and orientation of the tulip assembly 20 with respect to the pedicle screw 12. It will be readily apparent to those of ordinary skill in the art that other means could be used to drive the wedges 32, 34 or another compressive structure into the compressible cup 30 or other sleeve structure, causing it to exert a securing force on the screw head 16.

The tulip assembly 20 further includes an inner set screw 42, optionally threaded through the outer set screw 40, that is operable to "lock" the rod 22 to the wedges 32, 34 through notches 44 manufactured or otherwise disposed the wedges 32, 34, or otherwise "lock" the rod 22 within the now immobilized tulip assembly 20. Of note, the rod 22 is not required to itself apply a force to the screw head 16, thereby eliminating the requirement for the rod 22 to be positioned or placed prior to "locking in" a desired angle of the tulip assembly 20.

Advantageously, the wedges 32, 34 and the compressible cup 30 enable the pedicle screw system 10 to be lock at a desired angle without requiring the rod 22 to be "locked" in place. Additionally, the compressible cup 30 provides a better locking mechanism than other conventional systems by enabling the force from the wedges 32, 34 to be evenly distributed to the screw head 16 as opposed to only on a top portion of the screw head 16. It will be readily apparent to those of ordinary skill in the art that the compressible cup 30 can have a variety of configurations and can cover any desired percentage of the surface of the compressible cup 30, and the wedges 32, 34 can concentrically cover any desired percentage of the interior circumference of the tulip assembly 20.

FIG. 2 illustrates an expanded view of all of the components of the pedicle screw system 10 according to one exemplary embodiment of the present invention. In assembly/operation, the compressible cup 30 is placed over the bone screw 14 to the screw head 16. Next, the tulip assembly 20 is placed over the bone screw 14 without the wedges 32, 34. The wedges 32, 34 are then placed within the tulip assembly 20. The bone screw 14 is secured to a pedicle or the like, and the outer set screw 40 is utilized to position a desired angle of the pedicle screw system 10, "locking" the pedicle screw 12 in place through the compressible cup 30 and the wedges 32, 34. Finally, the rod 22 is positioned and "locked" in place with the inner set screw 42.

Figure 3:
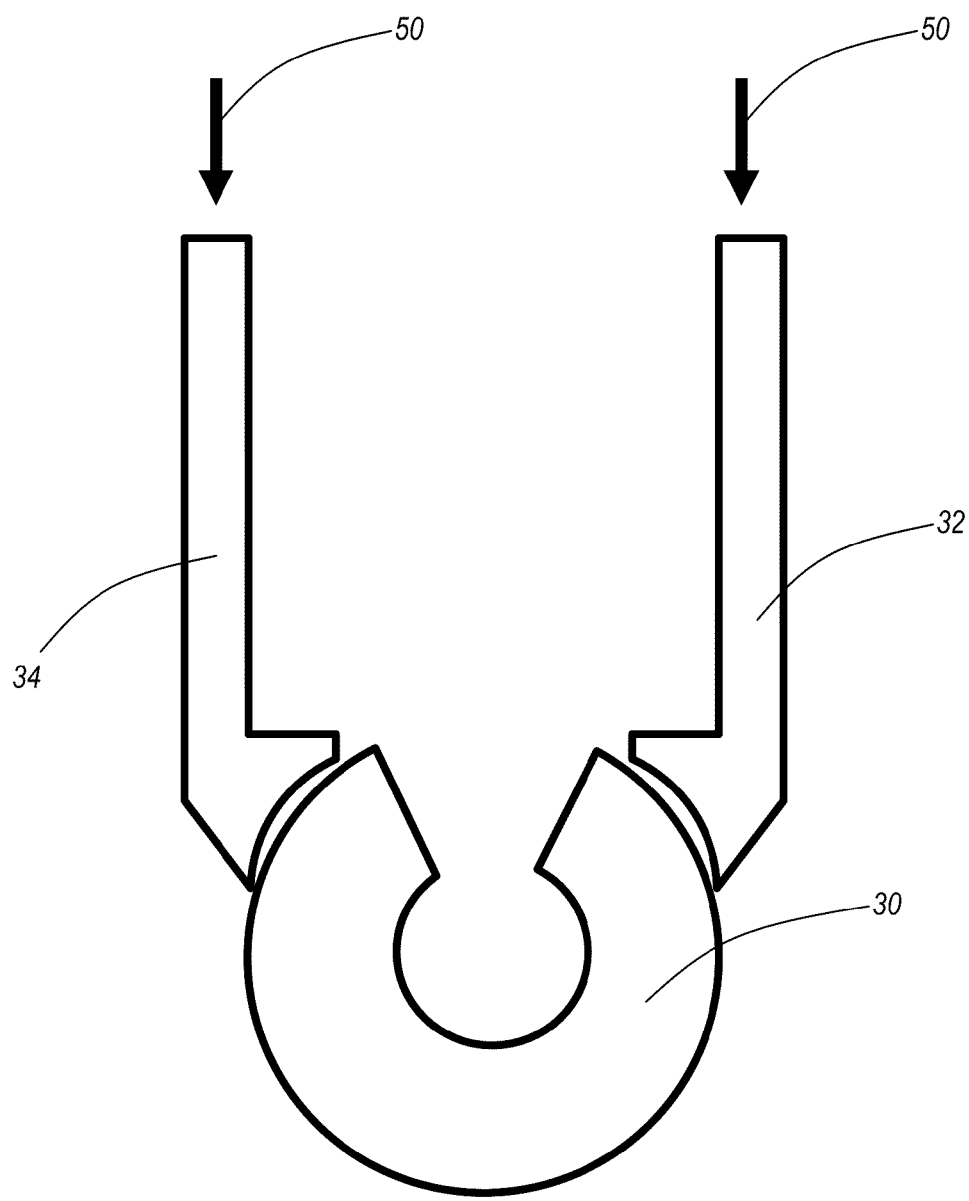
FIG. 3 is a partial cross-sectional diagram of a compressible cup and wedge structures of the pedicle or other surgical screw system of FIG. 1, according to one exemplary embodiment of the present invention.

Referring to FIG. 3, the compressible cup 30 and the wedges 32, 34 are illustrated according to one exemplary embodiment of the present invention. The outer set screw 40 (not shown in FIG. 3) is configured to exert a force 50 on each of the wedges 32, 34. This force 50 is translated to the compressible cup 30, causing the compressible cup 30 to tightly "form" around the screw head 16 (not shown in FIG. 3). Accordingly, the present invention ensures the tulip assembly 20 (not shown in FIG. 3) is "locked" in place to the screw head 16, and not solely "locked" to a top of the screw head 16.

Figure 4:
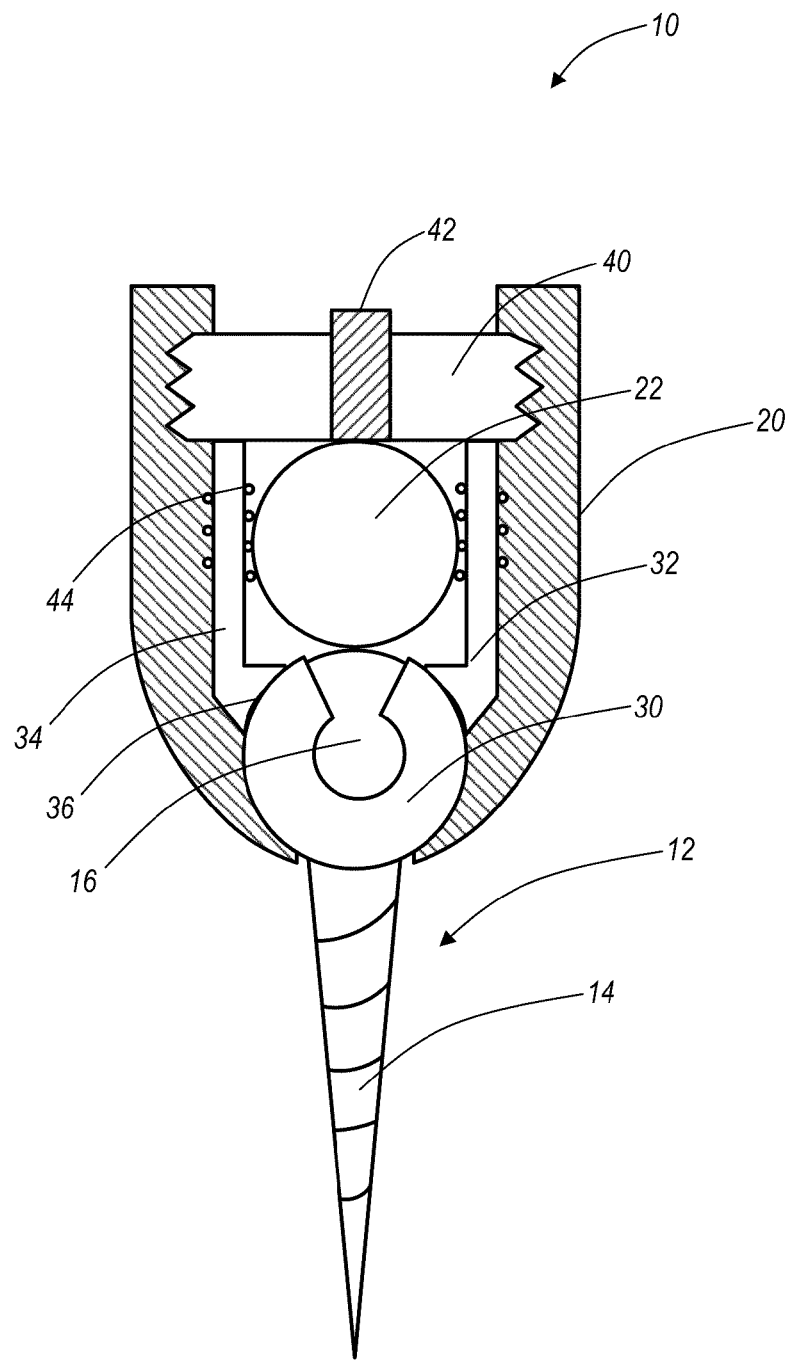
FIG. 4 is a partial cross-sectional diagram of the pedicle or other surgical screw system of FIG. 1 in a fully-engaged configuration, according to one exemplary embodiment of the present invention.

Referring to FIG. 4, the pedicle screw system 10 is illustrated in a fully deployed configuration according to one exemplary embodiment of the present invention. Here, the wedges 32, 34 are disposed tightly between the outer set screw 40 and the compressible cup 30, thereby locking the tulip assembly 20 to the pedicle screw 12. The rod 22 is positioned within the tulip assembly 20, locked in place by the inner set screw 42, the wedges 32, 34, and the screw head 16.

Those of ordinary skill in the art will recognize that the pedicle screw system 10 can operate as either monoaxial or polyaxial, selectively and alternatively. Further, multiple pedicle screw systems 10 can be used together to secure the rod 22 or a plurality of rods 22.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. A surgical screw system, comprising:
a surgical screw comprising a head portion and a threaded portion;
a compressible sheath configured to engage at least a portion of the head portion of the surgical screw, wherein the compressible sheath comprises a first curved surface;
a tulip assembly, wherein the head portion of the surgical screw is configured to be disposed within the tulip assembly; and
a compression structure configured to be disposed within the tulip assembly, wherein the compression structure comprises a second curved surface, wherein the second curved surface is configured to at least substantially mate with the first curved surface, and wherein the compression structure is configured for selectively compressing the compressible sheath about the head portion of the surgical screw, thereby securing the head portion of the surgical screw in place within the tulip assembly.

2. The surgical screw system of claim 1, wherein the head portion of the surgical screw has a substantially spherical shape and at least a portion of the compressible sheath has an at least substantially spherical shape.

3. The surgical screw system of claim 1, further comprising a stabilizing member configured to be disposed partially within the tulip assembly and having a primary axis substantially perpendicular to a primary axis of the threaded portion of the surgical screw.

4. The surgical screw system of claim 3, wherein the compression structure is configured to be disposed concentrically within the tulip assembly on opposing sides of the stabilizing member.

5. The surgical screw system of claim 3, further comprising an outer set screw configured to be threadedly disposed within the tulip assembly, wherein the outer set screw is configured for selectively compressing the compression structure against the compressible sheath to compress the compressible sheath about the head portion of the surgical screw, thereby securing the head portion of the surgical screw in place within the tulip assembly.

6. The surgical screw system of claim 5, further comprising an inner set screw configured to be threadedly disposed with the outer set screw, wherein the inner set screw is configured for selectively securing the stabilizing member in place within the tulip assembly.

7. The surgical screw system of claim 1, further comprising:
an outer set screw; and
an inner set screw configured to be threadably received within the outer set screw.

8. The surgical screw system of claim 7, further comprising a stabilizing member configured to be disposed within the tulip assembly and having a primary axis substantially perpendicular to a primary axis of the threaded portion of the surgical screw, wherein the inner set screw is configured to fix the stabilizing member is place, and wherein the outer set screw is configured to fix the surgical screw in place.

9. The surgical screw system of claim 8, wherein the inner set screw is configured to selectively contact the stabilizing member to fix the stabilizing member in place, and wherein the outer set screw is configured to selectively contact the compression structure to compress the compressible sheath about the head portion of the surgical screw.

10. The surgical screw system of claim 8 wherein, prior to actuation of the outer set screw, the surgical screw is configured to be polyaxial relative to the tulip assembly, and wherein the outer set screw is configured to selectively fix the surgical screw at a particular angle relative to the tulip assembly such that, after actuation of the outer set screw, the surgical screw is monoaxial relative to the tulip assembly.

11. The surgical screw system of claim 1, wherein the surgical screw is configured to initially be in a polyaxial configuration relative to the tulip assembly, and wherein surgical screw is configured to be selectively fixed at a particular angle relative to the tulip assembly such that, after selective fixation of the surgical screw, the surgical screw is in a monoaxial configuration relative to the tulip assembly.

12. The surgical screw system of claim 11, further comprising a stabilizing member configured to be disposed within the tulip assembly and having a primary axis substantially perpendicular to a primary axis of the threaded portion of the surgical screw, wherein the stabilizing member is configured to be fixed within the tulip assembly, and wherein the surgical screw is configured to be in the monoaxial configuration prior to fixing the stabilizing member within the tulip assembly.

13. The surgical screw system of claim 1, wherein the compressible sheath is configured to engage a lower portion of the head portion of the surgical screw.

14. The surgical screw system of claim 13, wherein the compressible sheath and the compression structure are configured such that the compressible sheath distributes force from the compression structure evenly about the head portion of the surgical screw.

15. The surgical screw system of claim 1, wherein the compressible sheath is configured to extend around the head portion such that at least a portion of the compressible sheath engages a lower portion of the head portion and at least a portion of the compressible sheath engages an upper portion of the head portion.

16. The surgical screw system of claim 1, further comprising:
a stabilizing member configured to be disposed partially within the tulip assembly and having a primary axis substantially perpendicular to a primary axis of the threaded portion of the surgical screw, wherein the stabilizing member is configured to be engaged with the compression structure in order to lock the stabilizing member in place relative to the tulip assembly.

17. The surgical screw system of claim 16, wherein the compression structure comprises at least one notch configured for engagement with the stabilizing member in order to lock the stabilizing member in place relative to the tulip assembly.

18. The surgical screw system of claim 17, wherein the compression structure is configured to prevent the stabilizing member from directly contacting the head portion.

19. The surgical screw system of claim 17, wherein the compression structure comprises a plurality of notches configured for engagement with the stabilizing member in order to lock the stabilizing member in place relative to the tulip assembly.

20. A pedicle screw system, comprising:
a pedicle screw comprising a head portion and a threaded portion;
a compressible cup configured to engage at least a portion of the head portion of the pedicle screw, wherein the compressible cup is configured to extend around the head portion such that at least a portion of the compressible cup engages a lower portion of the head portion and at least a portion of the compressible cup engages an upper portion of the head portion;
a tulip assembly, wherein the head portion of the pedicle screw is configured to be disposed within the tulip assembly; and
a wedge member configured to be disposed within the tulip assembly, wherein the wedge member is configured for selectively compressing the compressible cup about the head portion of the pedicle screw, thereby securing the head portion of the pedicle screw in place within the tulip assembly.

21. The pedicle screw system of claim 20, wherein the head portion of the pedicle screw has a substantially spherical shape and at least a portion of the compressible cup has an at least substantially spherical shape.

22. The pedicle screw system of claim 20, further comprising a stabilizing member configured to be disposed partially within the tulip assembly and having a primary axis substantially perpendicular to a primary axis of the threaded portion of the pedicle screw.

23. The pedicle screw system of claim 22, wherein the wedge member is configured to be disposed concentrically within the tulip assembly on opposing sides of the stabilizing member.

24. The pedicle screw system of claim 22, further comprising an outer set screw configured to be threadedly disposed within the tulip assembly, wherein the outer set screw is configured for selectively compressing the wedge member against the compressible cup to compress the compressible cup about the head portion of the pedicle screw, thereby securing the head portion of the pedicle screw in place within the tulip assembly.

25. The pedicle screw system of claim 24, further comprising an inner set screw configured to be threadedly disposed with the outer set screw, wherein the inner set screw is configured for selectively securing the stabilizing member in place within the tulip assembly.

26. The pedicle screw system of claim 20, wherein the wedge member comprises a first curved surface, wherein the compressible cup comprises a second curved surface, and wherein the second curved surface is configured to at least substantially mate with the first curved surface.

27. The pedicle screw system of claim 20, wherein the system is configured such that the compressible cup extends around at least a majority of a perimeter of the head portion when the compressible cup is engaged with the head portion.

28. The pedicle screw system of claim 20, wherein the system is configured such that the wedge member converts a downward force received by the wedge member into a plurality of forces each directed at least substantially towards a center of the head portion.

29. The pedicle screw system of claim 28, further comprising a set screw configured to engage the wedge member in order to generate the downward force.

30. The pedicle screw system of claim 20, further comprising a second wedge member configured to be disposed within the tulip assembly, wherein the second wedge member is configured for selectively compressing the compressible cup about the head portion of the pedicle screw, thereby securing the head portion of the pedicle screw in place within the tulip assembly.

31. The pedicle screw system of claim 30, wherein the second wedge member is configured to be positioned within the tulip assembly adjacent to a side of the tulip assembly opposite from the wedge member.

* * * * *